(12) United States Patent
Mhaske et al.

(10) Patent No.: US 9,200,018 B2
(45) Date of Patent: Dec. 1, 2015

(54) PROCESS FOR PREPARATION OF ARYL PHOSPHOROUS COMPOUNDS

(71) Applicant: Council of Scientific & Industrial Research, New Delhi (IN)

(72) Inventors: Santosh Baburao Mhaske, Maharashtra (IN); Ranjeet Ashokrao Dhokale, Maharashtra (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 14/419,978

(22) PCT Filed: Aug. 6, 2013

(86) PCT No.: PCT/IN2013/000484
§ 371 (c)(1),
(2) Date: Feb. 6, 2015

(87) PCT Pub. No.: WO2014/024212
PCT Pub. Date: Feb. 13, 2014

(65) Prior Publication Data
US 2015/0210725 A1    Jul. 30, 2015

(30) Foreign Application Priority Data

Aug. 6, 2012 (IN) .......................... 2444/DEL/2012
Dec. 21, 2012 (IN) .......................... 3957/DEL/2012

(51) Int. Cl.
| C07F 9/6561 | (2006.01) |
| C07F 9/655 | (2006.01) |
| C07F 9/40 | (2006.01) |
| C07F 9/32 | (2006.01) |
| C07F 9/53 | (2006.01) |

(52) U.S. Cl.
CPC .......... *C07F 9/65517* (2013.01); *C07F 9/3229* (2013.01); *C07F 9/4021* (2013.01); *C07F 9/5325* (2013.01)

(58) Field of Classification Search
CPC ................................................. C07F 9/65522
See application file for complete search history.

(56) References Cited

PUBLICATIONS

International Search Report and the Written Opinion of the International Searching Authority, PCT/IN2013/000484, Council of Scientific & Industrial Research, Nov. 20, 2013.
Yang, Guoqiang et al., Nickel-catalyzed Arbuzov reactions of aryl triflates with triethyl phosphite, Tetrahedron Letters 52 (2011), pp. 5032-5035.
Remond, Emmanuelle et al., Efficient Synthesis of Quaternary and P-Stereogenic Phosphonium Triflates, Organic Letters, 2010, vol. 12, No. 7, pp. 1568-1571.
Dhokale, Ranjeet A. et al., P-Arylation: Arynes to Aryl-Phosphonates, -Phosphinates, and -Phosphine Oxides, Organic Letters, 2013, vol. 15, No. 9, pp. 2218-2221.
Yoshida, Suguru et al., Synthesis of Diverse Aromatic Oxophosphorus Compounds by the Michaelis-Arbuzov-type Reaction of Arynes, The Chemical Society of Japan, Chem. Lett. 2013, 42, pp. 583-585.

*Primary Examiner* — Sun Jae Yoo
(74) *Attorney, Agent, or Firm* — McDonald Hopkins LLC

(57) ABSTRACT

The present invention relates to cost effective, transition-metal-free one pot process for the preparation of aryl phosphorous compounds of formula (I). Particularly, the present invention provides a process for C—P bond formation. In particular, the invention relates to mild fluoride induced generation of aryne species in situ which allows P—C bond formation to obtain aryl phosphorous compounds of formula (I) under mild condition.

8 Claims, 3 Drawing Sheets

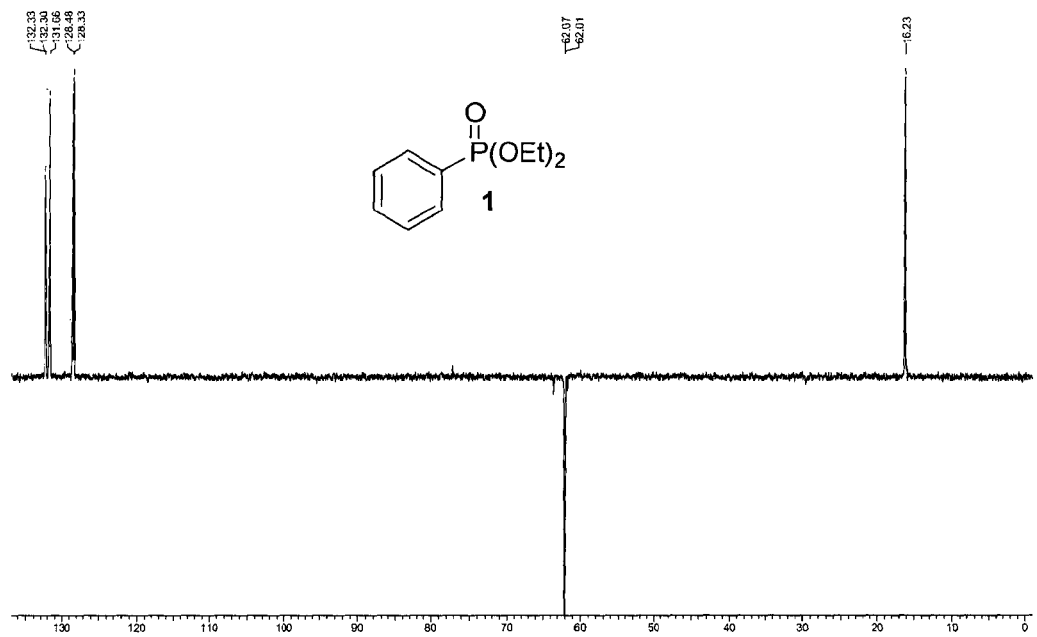
Representative spectra of $^{13}$CMR DEPT of Phosphonate (1)
Figure: 1

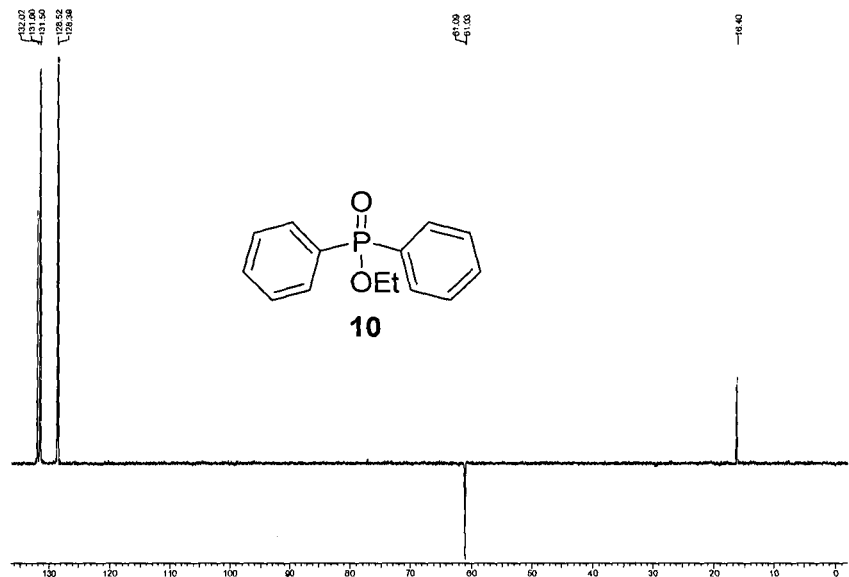
Representative spectra of $^{13}$CMR DEPT of Phosphinate (10)
Figure: 2

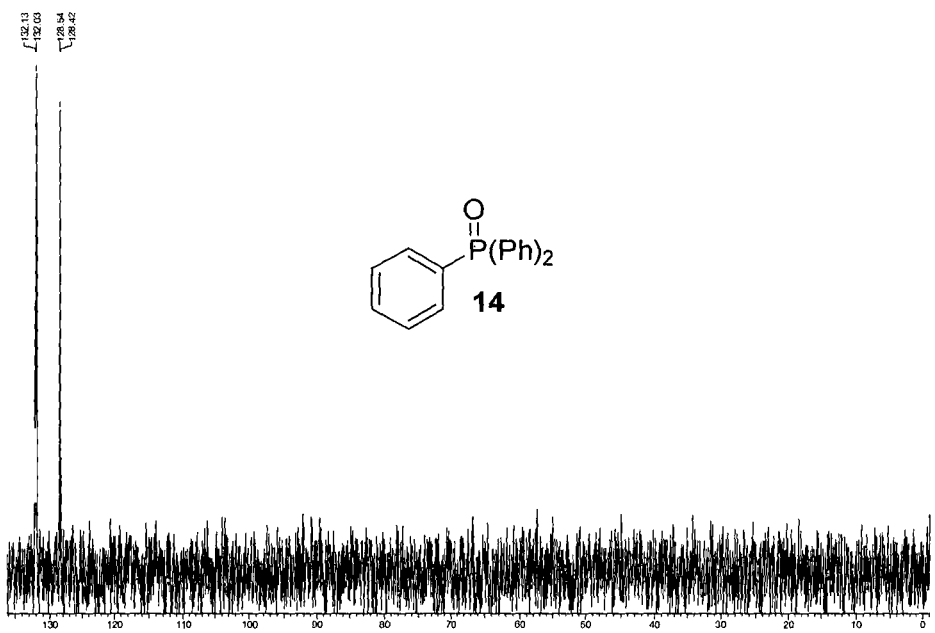
Representative spectra of $^{13}$CMR DEPT of Phosphine oxide (14)
Figure: 3

PROCESS FOR PREPARATION OF ARYL PHOSPHOROUS COMPOUNDS

FIELD OF THE INVENTION

The present invention relates to cost effective, transition-metal-free one pot process for the preparation of aryl phosphorous compounds of formula (I). Particularly, the present invention provides a process for C—P bond formation. In particular, the invention relates to use of mild, fluoride induced generation of aryne species in situ which allows P—C bond formation to obtain aryl phosphorous compounds of formula (I) under mild condition.

BACKGROUND OF THE INVENTION

Aryl and hetero-aryl phosphorous compounds including phosphonates, phosphinites and phosphine oxides are valuable intermediates in organic synthesis and find applications in organic synthesis, polymers, medicinal chemistry and nucleic acid chemistry. Several methods are known in the art for the synthesis of aryl, hetero-aryl phosphorous compounds. Michaelis-Arbuzov reaction (also called the Arbuzov reaction) which is frequently used involves a reaction of trialkyl phosphite and an alkyl halide to form a phosphonate, however the methodology for the synthesis of aryl phosphonates was limited due to poor reactivity of aryl halides until Hirao developed palladium catalyzed coupling of arylhalides with hydrogen-phosphonates. Several other metal catalyzed processes were developed for the C—P bond forming reactions for synthesis of aryl phosphonates.

An article titled "Copper-Catalyzed C—P Bond Construction via Direct Coupling of Phenylboronic Acids with H-Phosphonate Diesters" by Rongqiang Zhuang, Jian Xu et. al in Organic Letters 2011 Vol. 13, No. 8 pg. nos 2110-2113 discloses copper-catalyzed reaction of H-phosphonate diesters to boronic acids under the copper catalyst system $Cu_2O$/1,10-phenanthroline to form aryl phosphonates.

Recently, oxidative phosphorylation of arylboronic acids catalyzed by palladium or copper has been revealed.

The utilization of aryl triflates as substrates was found attractive in organic reactions, since the phenol derivatives are readily available and may be used as a directing group for the introduction of other functional groups on the aromatic ring, thus allowing access to wider substrate scope.

An article titled "Nickel-catalyzed Arbuzov reactions of aryl triflates with triethyl phosphite" by Guoqiang Yang, Chaoren Shen et. al in Tetrahedron Letters 52 (2011) 5032-5035 relate to nickel-catalyzed phosphorylation of aryl triflates with triethyl phosphite, in which KBr as an additive promoted the $SN_2$ catalytic step. The reaction is carried out at a temperature in the range of 185-190° C. for about 20 hours.

While the processes in the art generate the desired aryl phosphonates, however, the reactions include reactants which are costly such as expensive phosphorous containing ligands, require the use of organic or inorganic bases, transition metal catalysts and the reactions typically proceed at high temperature and involve longer time.

Arynes are known as extremely useful reactive intermediate in organic synthesis. As it is kinetically unstable, highly strained molecule it can readily undergo addition reactions. Key consideration in the development of aryne chemistry is the generation of the reactive intermediate and its precursor. Various methods are known for the production of arynes. A mild and effective method to form a aryne intermediate is to use fluoride induced ortho elimination of o-(trimethylsilyl) aryl triflates which can be easily prepared with various substituents on the arene ring. Thesis titled 'Development of Versatile Strategies for Aryne Annulation, Applications In Methodology And Natural Product Total Synthesis' 2010 by Kevin McCormack Allan, also mentions the generation of benzyne by a method developed by Kobayashi and co-workers which involves fluoride induced ortho elimination of o-(trimethylsilyl)aryl triflates.

However, the preparation of aryl phosphorous compounds via arynes at milder conditions is not known.

With a view to develop a facile process for the synthesis of aryl phosphorous compounds, which is convenient, inexpensive and ameliorates the drawbacks of the prior art processes, the present inventors piloted their scope of invention in the synthesis of aryl phosphorous compounds via generation of aryne intermediate from silyl triflates.

OBJECTS OF THE INVENTION

An object of the invention is to provide transition metal free, one pot efficient process for the synthesis of aryl phosphorous compounds of formula (I).

Another object of the invention is to provide a process for C—P bond formation.

Another object of the invention is to use mild fluoride induced generation of aryne species in situ which allows P—C bond formation to obtain aryl phosphorous compounds of formula (I) under mild condition

SUMMARY OF THE INVENTION

Accordingly, the present invention provides a one pot process for the preparation of aryl phosphorous compound of formula (I) comprising reacting o-(trimethylsilyl) aryl triflates (formula II) with phosphorous compound of formula (III) in presence of CsF in polar solvent at room temperature ranging between 25-35° C. under stirring for a period ranging between 4-35 h, concentrating and purifying to obtain aryl phosphorous compound of formula (I);

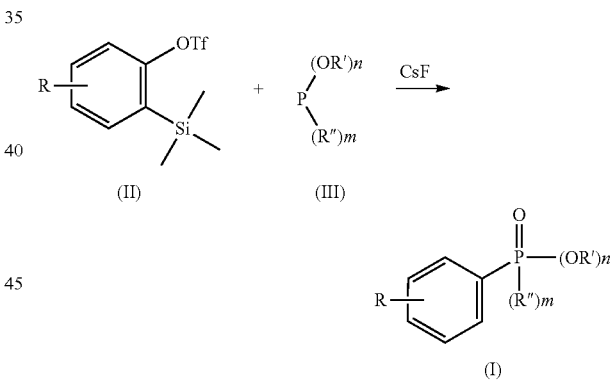

wherein, R represents hydrogen, alkyl, alkenyl, alkynyl, halo, hydroxy, alkoxy, (un)substituted or substituted aryl, benzyl, (un)substituted or substituted heteroaryl, oxalane group, —O—$CH_2$—$CH_2$—O—; N—R R' and R" represent alkyl, benzyl, alkenyl, alkynyl, (un)substituted or substituted aryl, (un)substituted or substituted heteroaryl;

'n' is 0-2; 'm' is 0-2;

with the proviso, when 'm' is 0, 'n' is 2; R represents hydrogen, alkyl, alkenyl, alkynyl, halo, hydroxy, alkoxy, (un)substituted or substituted aryl, benzyl, (un)substituted or substituted heteroaryl, oxalane group, —O—$CH_2$—$CH_2$—O, N—R and R' represent alkyl, benzyl, alkenyl, alkynyl, (un) substituted or substituted aryl, (un)substituted or substituted heteroaryl;

with the proviso, when 'n' is 1, 'm' is 1; R represents hydrogen, alkyl, alkenyl, alkynyl, halo, hydroxy, alkoxy, (un)substituted or substituted aryl, benzyl, (un)substituted or substituted heteroaryl, oxalane group, —O—CH₂—CH₂—O, N—R and R" represent alkyl, benzyl, alkenyl, alkynyl, (un)substituted or substituted aryl, (un)substituted or substituted heteroaryl;

with the proviso, when 'n' is 0, 'm' is 2; R represents hydrogen, alkyl, alkenyl, alkynyl, halo, hydroxy, alkoxy, (un)substituted or substituted aryl, benzyl, (un)substituted or substituted heteroaryl, oxalane group, —O—CH₂—CH₂—O, N—R and R" represent alkyl, benzyl, alkenyl, alkynyl, (un)substituted or substituted aryl, (un)substituted or substituted heteroaryl.

In an embodiment of the present invention the aryl phosphorous compounds of formula (I) represented by following structures;

(1)
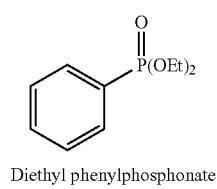
Diethyl phenylphosphonate (2)
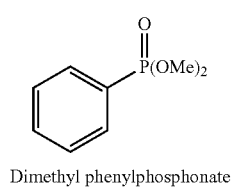
Dimethyl phenylphosphonate (3)
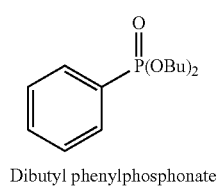
Dibutyl phenylphosphonate (4)
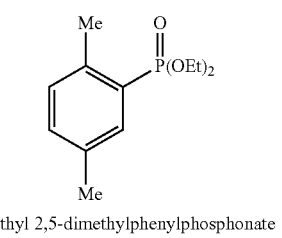
Diethyl 2,5-dimethylphenylphosphonate (5)
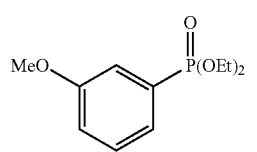
Diethyl 3-methoxyphenylphosphonate (6)
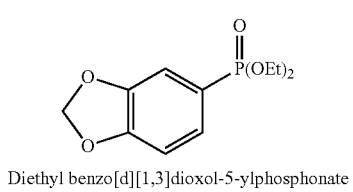
Diethyl benzo[d][1,3]dioxol-5-ylphosphonate (7)
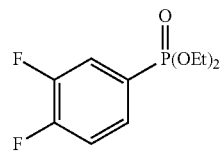
Diethyl 3,4-difluorophenylphosphonate (8)
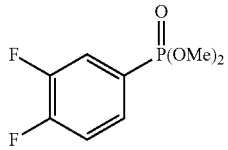
Dimethyl 3,4-difluorophenylphosphonate (9)
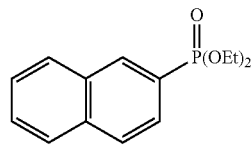
Diethyl naphthalen-2-ylphosphonate

(10)
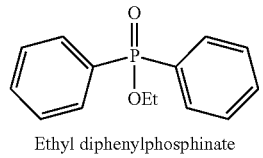
Ethyl diphenylphosphinate

(11)
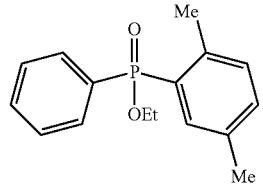
Ethyl(2,5-dimethylphenyl(phenyl)phosphinate

(12)
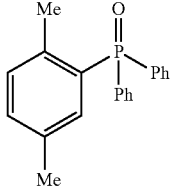
(2,5-dimethylphenyl)diphenylphosphine oxide)

(13)
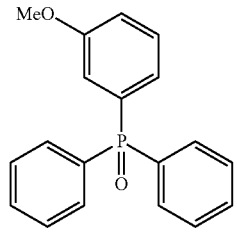
(3-methoxyphenyl)diphenylphosphine oxide

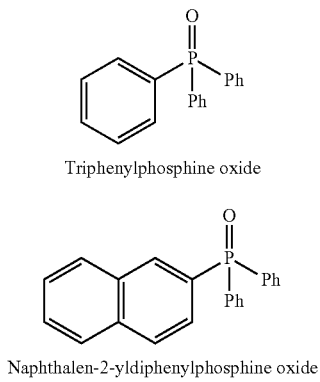

Triphenylphosphine oxide (14)

Naphthalen-2-yldiphenylphosphine oxide (15)

In one embodiment of the present invention mole ratio of o-(trimethylsilyl) aryl triflates (formula II) and phosphorous compound of formula (III) is in the range of 1:4.

In another embodiment of the present invention polar solvent used is selected from the group consisting of acetonitrile, Tetrahydrofuran (THF), 1,4-Dioxane, dichloromethane, dichloroethane, butyronitrile, N,N-Dimethylformamide.

In another embodiment of the present invention yield of aryl phosphorous compounds of formula (I) is in the range of 62-96%.

In another embodiment of the present invention the process is transition-metal-free.

In another embodiment of the present invention the process involves generation of aryne in situ.

In another embodiment of the present invention aryl phosphorous compounds of formula (I) is useful as precursors to prepare aryl-phosphine ligands.

BRIEF DESCRIPTION OF ACCOMPANYING DRAWINGS

FIG. 1 depicts representative spectra for $^{13}$CMR DEPT of Phosphonate (1)

FIG. 2 depicts representative spectra for $^{13}$CMR DEPT of Phosphinate (10)

FIG. 3 depicts representative spectra for $^{13}$CMR DEPT of Phosphine oxide (14)

DETAILED DESCRIPTION OF THE INVENTION

The present invention discloses cost effective, transition-metal-free, one pot process for the preparation of phosphorous compounds of formula (I) under mild conditions with generation of aryne species in situ as intermediate.

The invention uses a benzyne precursor, o-(trimethylsilyl) aryl triflates (formula II) which in presence of alkali metal fluoride can undergo desilylation and elimination to obtain benzyne, which allows synthesis of a wide range of aryl phosphorous compounds of formula (I).

In an embodiment, the present invention relates to a cost effective, transition-metal-free, one pot process for the preparation of aryl phosphorous compounds of formula (I) comprising reacting o-(trimethylsilyl) aryl triflates (formula II) with phosphorous compound of formula (III) in presence of CsF in polar solvent at room temperature, stirring until completion of reaction, concentrating and purifying, wherein said process involves generation of aryne in situ.

The process for preparation is shown below in Scheme I

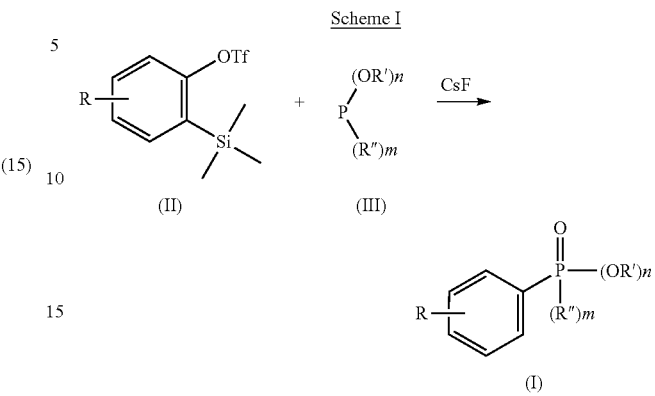

wherein, R represents hydrogen, alkyl, alkenyl, alkynyl, halo, hydroxy, alkoxy, (un)substituted or substituted aryl, benzyl, (un)substituted or substituted heteroaryl, oxalane group, —O—$CH_2$—$CH_2$—O—; N—R R' and R" represent alkyl, benzyl, alkenyl, alkynyl, (un)substituted or substituted aryl, (un)substituted or substituted heteroaryl;

For formula (I): 'n' is 0-2; 'm' is 0-2;

with the proviso, when 'm' is 0, 'n' is 2; R represents hydrogen, alkyl, alkenyl, alkynyl, halo, hydroxy, alkoxy, (un)substituted or substituted aryl, benzyl, (un)substituted or substituted heteroaryl, oxalane group, —O—$CH_2$—$CH_2$—O, N—R and R' represent alkyl, benzyl, alkenyl, alkynyl, (un)substituted or substituted aryl, (un)substituted or substituted heteroaryl;

with the proviso, when 'n' is 1, 'm' is 1; R represents hydrogen, alkyl, alkenyl, alkynyl, halo, hydroxy, alkoxy, (un)substituted or substituted aryl, benzyl, (un)substituted or substituted heteroaryl, oxalane group, —O—$CH_2$—$CH_2$—O, N—R and R" represent alkyl, benzyl, alkenyl, alkynyl, (un)substituted or substituted aryl, (un)substituted or substituted heteroaryl;

with the proviso, when 'n' is 0, 'm' is 2; R represents hydrogen, alkyl, alkenyl, alkynyl, halo, hydroxy, alkoxy, (un)substituted or substituted aryl, benzyl, (un)substituted or substituted heteroaryl, oxalane group, —O—$CH_2$—$CH_2$—O, N—R and R" represent alkyl, benzyl, alkenyl, alkynyl, (un)substituted or substituted aryl, (un)substituted or substituted heteroaryl.

The benzyne intermediate formed in situ reacts with phosphorous compound of formula (III) to yield compound of formula (I) as shown below:

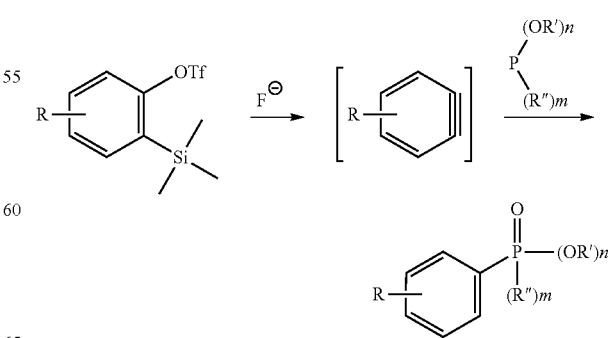

wherein, R, R', R", 'm' and 'n' are as defined hereinabove.

Accordingly, to a stirred solution of CsF in anhydrous acetonitrile is consecutively added benzyne precursor, o-(trimethylsilyl) aryl triflates (formula II) and phosphorous compound of formula (III). Reaction mixture is allowed to stir at room temperature for 1-36 hrs. The reaction mixture is concentrated and directly loaded on silica gel column and purified by using solvent gradient of Pet. Ether:Ethyl Acetate (1:1) to yield a colourless liquid of formula (I).

The phosphorous compound of formula (III) is selected from the group of phosphites, phosphonites and phosphinites.

In an embodiment, the present invention provides phosphorous compounds of formula (I);

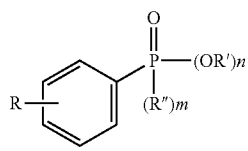

(I)

wherein, R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O—; N—R
R' and R" represent alkyl, benzyl, alkenyl, alkynyl, (un)substituted or substituted aryl, (un)substituted or substituted heteroaryl;
'n' is 0-2; 'm' is 0-2;
with the proviso, when 'm' is 0, 'n' is 2; R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O, N—R and R' represent alkyl, benzyl, alkenyl, alkynyl, (un)substituted or substituted aryl, (un)substituted or substituted heteroaryl;
with the proviso, when 'n' is 1, 'm' is 1; R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O, N—R and R" represent alkyl, benzyl, alkenyl, alkynyl, (un) substituted or substituted aryl, (un)substituted or substituted heteroaryl;
with the proviso, when 'n' is 0, 'm' is 2; R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O, N—R and R" represent alkyl, benzyl, alkenyl, alkynyl, (un) substituted or substituted aryl, (un)substituted or substituted heteroaryl.

The phosphorous compounds of formula (I) prepared by the process of instant invention comprises:

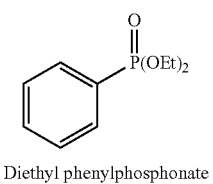

(1)

Diethyl phenylphosphonate

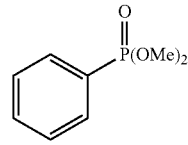

(2)

Dimethyl phenylphosphonate

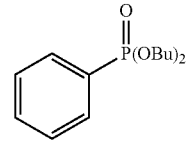

(3)

Dibutyl phenylphosphonate

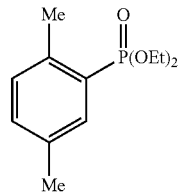

(4)

Diethyl 2,5-dimethylphenylphosphonate

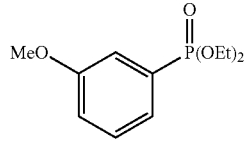

(5)

Diethyl 3-methoxyphenylphosphonate

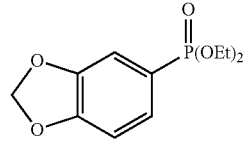

(6)

Diethyl benzo[d][1,3]dioxol-5-ylphosphonate

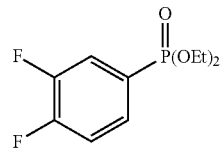

(7)

Diethyl 3,4-difluorophenylphosphonate

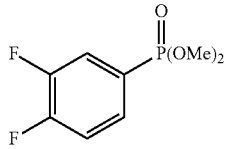

(8)

Dimethyl 3,4-difluorophenylphosphonate

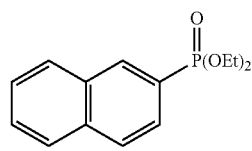

(9)

Diethyl naphthalen-2-ylphosphonate

-continued

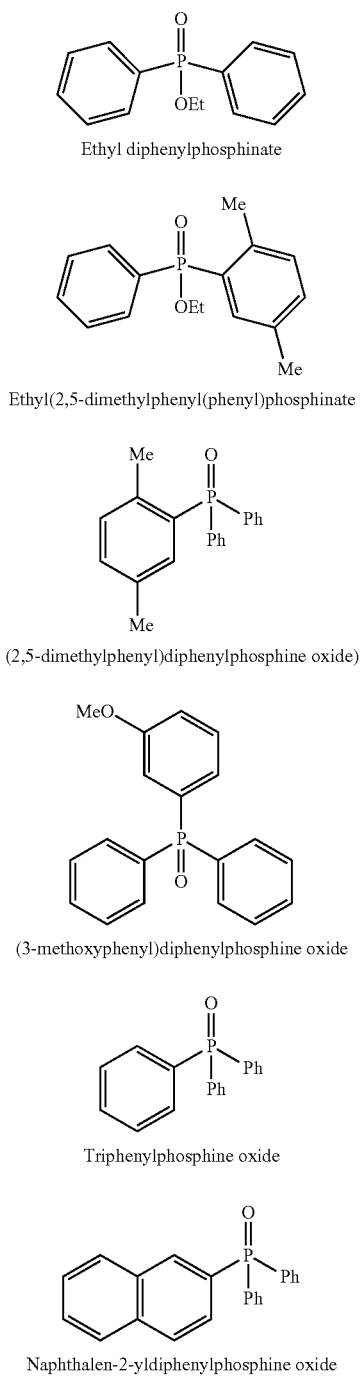

(10) Ethyl diphenylphosphinate

(11) Ethyl(2,5-dimethylphenyl(phenyl)phosphinate

(12) (2,5-dimethylphenyl)diphenylphosphine oxide)

(13) (3-methoxyphenyl)diphenylphosphine oxide

(14) Triphenylphosphine oxide

(15) Naphthalen-2-yldiphenylphosphine oxide

In an embodiment, the process of present invention provides regioselective, phosphorous compounds of formula (I).

In another embodiment, the present invention relates to cost effective, transition-metal-free, one pot process that involves generation of aryne in situ. The preparation of aryl phosphonates (compounds 1-9) comprises reacting o-(trimethylsilyl) aryl triflates (formula II) with phosphorous compound of formula (IV) in presence of CsF in polar solvent at room temperature, stirring until completion of reaction, concentrating and purifying to obtain desired product.

The process is shown below in Scheme II.

Scheme II (II) + P(OR')n → (CsF / CH3CN, r.t.) → compounds 1-9 (R, (OR')n)

wherein, R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O—, N—R R' represent—alkyl, benzyl, alkenyl, alkynyl, (un)substituted or substituted aryl, (un)substituted or substituted heteroaryl; and 'n' is 2.

In yet another embodiment, the present invention relates to cost effective, transition-metal-free, one pot process that involves generation of aryne in situ. The preparation of aryl phosphinates (compounds 10, 11) comprises reacting o-(trimethylsilyl) aryl triflates (formula II) with phosphorous compound of formula (V) in presence of CsF in polar solvent at room temperature, stirring until completion of reaction, concentrating and purifying to obtain desired product.

The process is shown below in Scheme III.

Scheme III (II) + (V) → (CsF / CH$_3$CN, r.t) → compounds 10, 11 wherein, R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O—, N—R; R' represent—alkyl, benzyl, alkenyl, alkynyl, (un)substituted or substituted aryl, (un)substituted or substituted heteroaryl; 'n' is 1.

In another embodiment, the present invention relates to cost effective, transition-metal-free, one pot process, that involves generation of aryne in situ. The preparation of phosphine oxides (compounds 12-15) comprises reacting o-(trimethylsilyl) aryl triflates (formula II) with phosphorous compound of formula (VI) in presence of CsF in polar solvent at room temperature, stirring until completion of reaction, concentrating and purifying to obtain desired product.

The process is shown below in Scheme IV.

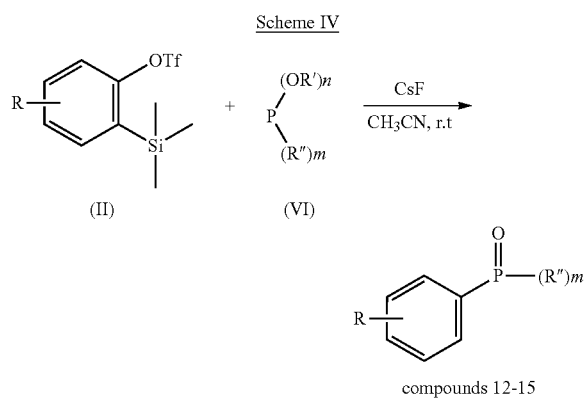

wherein, R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O—, N—R;
R' and R" represent alkyl, benzyl, alkenyl, alkynyl, (un)substituted or substituted aryl, (un)substituted or substituted heteroaryl; 'n' is 0; 'm' is 2.

In an embodiment, the present invention discloses diethyl 3,4-difluorophenylphosphonate of formula;

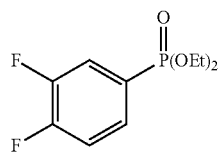

In another embodiment, the present invention discloses Ethyl (2,5-dimethylphenyl) (phenyl)phosphinate of formula;

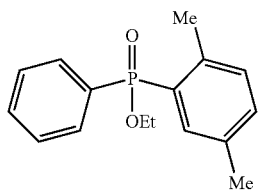 [SMILES: CCOP(=O)(c1ccccc1)c1cc(C)ccc1C]

The aryl phosphorous compound of formula (I) obtained by the process of the instant invention are further characterized.

The instant process is advantageous as it is simple, efficient, regioselective, one pot and the use of benzyne intermediate affords the process to take place under milder conditions.

The following examples are given by way of illustration of the present invention and therefore should not be construed to limit the scope of the invention.

EXAMPLES

Following examples are given by way of illustration therefore should not be construed to limit the scope of the invention.

Example 1

General Experimental Procedure for the Phosphorylation

To a flame dried two-neck round-bottom flask containing CsF (5.50 equiv.) was added o-silyl aryl triflate (II) (1.00 equiv.) in acetonitrile, followed by addition of phosphorous compound of formula (III) (4.00 equiv.) in acetonitrile under argon atmosphere. The reaction mixture was stirred at room temperature and the progress was monitored by TLC. After completion of the reaction, acetonitrile was removed on rotary evaporator and the crude product was dried under high vacuum and purified by flash silica gel column using a gradient of ethyl acetate-petroleum ether to afford corresponding aryl-phosphorous compounds of formula (I) in good to excellent yields.

Example 2

Synthesis of Diethyl Phenylphosphonate (1)

To a stirred solution of CsF (Cesium Fluoride, 1.4 g, 9.22 mmol) in anhydrous acetonitrile (5 mL) was consecutively added o-trimethylsilyl phenyl triflate (500 mg, 1.67 mmol) and triethyl phosphite (1.12 g, 6.71 mmol). Reaction mixture was allowed to stir at room temperature (30° C.) for 20 hrs. The reaction mixture was concentrated and directly loaded on silica gel column and purified by using solvent gradient of Pet. Ether:Ethyl Acetate (1:1) to yield a colourless liquid phosphonate 1 (345 mg, 96%).

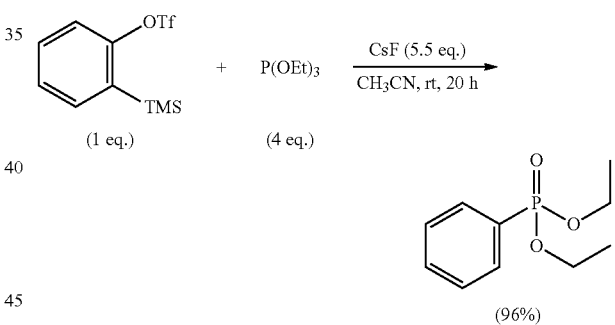

Reaction Time: 20 h, Rf: 0.4 (1:1 EtOAc:Pet. Ether); Thick oil; 345 mg, 96%; $^1$H NMR (400 MHz, CDCl$_3$, TMS) δ 7.88-7.77 (m, 2H), 7.60-7.52 (m, 1H), 7.51-7.43 (m, 2H), 4.22-4.02 (m, 4H), 1.33 (t, J=7.2 Hz, 6H); $^{13}$C NMR (100 MHz, CDCl$_3$, TMS) δ 132.3 (d, J=2.3 Hz), 131.7 (d, J=10.0 Hz), 128.4 (d, J=14.6 Hz), 128.3 (d, J=188.0 Hz), 62.0 (d, J=5.4 Hz), 16.3 (d, J=6.2 Hz); $^{31}$P NMR (162 MHz, CDCl$_3$) δ 18.8; Mass (M+Na)$^+$ 237; Known compound, Lit. M. Kalek, A. Ziadi, J. Stawinski, *Org. Lett.* 2008, 10, 4637.

Example 3

Synthesis of Dimethyl Phenylphosphonate (2)

To a stirred solution of CsF (112 mg, 0.74 mmol) in anhydrous acetonitrile was consecutively added o-trimethylsilyl phenyl triflate (40 mg, 0.13 mmol) and trimethyl phosphite (67 mg, 0.53 mmol). Reaction mixture was allowed to stir at room temperature (30° C.) for 16 hrs. The reaction mixture was concentrated and directly loaded on silica gel column and purified by using solvent gradient of Pet. Ether:Ethyl Acetate (1:1) to yield a colourless liquid phosphonate 2 (22 mg, 90%).

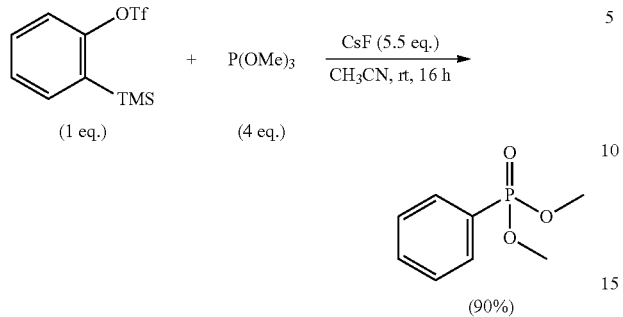

(90%)

Reaction Time: 16 h; Rf: 0.4 (1:1 EtOAc:Pet. Ether); Thick oil; 22.0 mg, 90%; $^1$H NMR (500 MHz, CDCl$_3$, TMS) δ 7.80 (dd, J=8.2, 13.4 Hz, 2H), 7.60-7.55 (m, 1H), 7.51-7.46 (m, 2H), 3.78 (s, 3H), 3.76 (s, 3H); $^{13}$C NMR (125 MHz, CDCl$_3$, TMS) δ 132.6 (d, J=2.9 Hz), 131.8 (d, J=9.5 Hz), 128.5 (d, J=15.3 Hz), 126.9 (d, J=188.8), 52.6 (d, J=5.7 Hz); $^{31}$P NMR (162 MHz, CDCl$_3$) δ 21.7; Mass (M+Na)$^+$ 209; Known compound, Lit. M. Kalek, A. Ziadi, J. Stawinski, *Org. Lett.* 2008, 10, 4637.

Example 4

Dibutyl Phenylphosphonate (3)

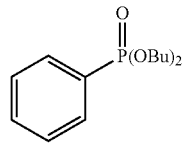

2-(trimethylsilyl)phenyl trifluoromethanesulfonate (25 mg, 0.083 mmol), Cesium Fluoride (70 mg, 0.461 mmol), Tributyl phosphite (83 mg, 0.335 mmol), Acetonitrile (1 ml): Reaction Time: 24 h; Rf: 0.4 (1:3 EtOAc:Pet. Ether); Thick oil; 16.3 mg, 72%; $^1$H NMR (400 MHz, CDCl$_3$, TMS) δ 7.80 (dd, J=6.8, 13.3 Hz, 2H), 7.55 (t, J=7.5 Hz, 1H), 7.50-7.42 (m, 2H), 4.12-3.95 (m, 4H), 1.65 (quint, J=7.3 Hz, 4H), 1.39 (sext, J=7.3 Hz, 4H), 0.9 (t, J=7.3 Hz, 6H); $^{13}$C NMR (100 MHz, CDCl$_3$, TMS) δ 132.3 (d, J=3.1 Hz), 131.7 (d, J=9.3 Hz), 128.4 (d, J=15.4 Hz), 128.3 (d, J=187.3 Hz), 65.8 (d, J=5.4 Hz), 32.4 (d, J=6.9 Hz), 18.7, 13.6; $^{31}$P NMR (162 MHz, CDCl$_3$) δ 18.8; Mass (M+Na)$^+$ 293; Known compound, Lit. X. Lu, J. Zhu, *Synthesis* 1987, 8, 726.

Example 5

Diethyl 2,5-dimethylphenylphosphonate (4)

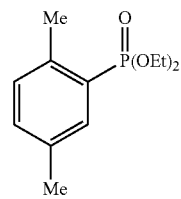

3,6-dimethyl-2-(trimethylsilyl)phenyl trifluoromethanesulfonate (25 mg, 0.076 mmol), Cesium Fluoride (64 mg, 0.421 mmol), Triethtyl phosphite (50 mg, 0.306 mmol), Acetonitrile (1 ml): Reaction Time: 35 h; Rf: 0.3 (1:4 EtOAc:Pet. Ether); Thick oil; 16.1 mg, 87%; $^1$H NMR (400 MHz, CDCl$_3$, TMS) δ 7.75 (d, J=14.8, 1 H), 7.23 (d, J=7.8 Hz, 1H), 7.17-7.10 (m, 1H), 4.21-4.00 (m, 4H), 2.52 (s, 3H), 2.34 (s, 3H), 1.33 (t, J=7.3 Hz, 6H); $^{13}$C NMR (100 MHz, CDCl$_3$, TMS) δ 138.5 (d, J=10.0 Hz), 134.9 (d, J=14.6 Hz), 134.5 (d, J=10.8 Hz), 133.2, 131.1 (d, J=15.4 Hz), 126.3 (d, J=182.7 Hz), 61.8 (d, J=5.4 Hz), 20.7, 20.6, 16.3 (d, J=6.2 Hz); $^{31}$P NMR (162 MHz, CDCl$_3$) δ 20.0; Mass (M+Na)$^+$ 265; Known Compound, Lit. S. Branion, V. Benin, *Synth. Commun.* 2006, 36, 2121.

Example 6

Diethyl 3-methoxyphenylphosphonate (5)

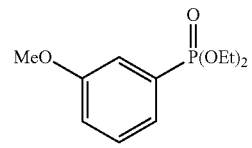

3-methoxy-2-(trimethylsilyl)phenyl trifluoromethanesulfonate (25 mg, 0.076 mmol), Cesium Fluoride (63 mg, 0.419 mmol), Triethtyl phosphite (50 mg, 0.304 mmol), Acetonitrile (1 ml): Reaction Time: 24 h; Rf: 0.3 (2:3 EtOAc:Pet. Ether); Thick oil; 13.7 mg, 74%; $^1$H NMR (200 MHz, CDCl$_3$, TMS) δ 7.45-7.28 (m, 3H), 7.15-7.01 (m, 1H), 4.25-3.96 (m, 4H), 3.85 (s, 3H), 1.33 (t, J=7.1 Hz, 6H); $^{13}$C NMR (100 MHz, CDCl$_3$, TMS) δ 159.4 (d, J=18.5 Hz), 129.7 (d, J=17.7 Hz), 129.6 (d, J=187.3 Hz), 124.0 (d, J=9.3 Hz), 118.8 (d, J=3.1 Hz), 116.4 (d, J=11.6 Hz), 62.2 (d, J=5.4 Hz), 55.41, 16.3 (d, J=6.2 Hz); $^{31}$P NMR (162 MHz, CDCl$_3$) δ 18.7; Mass (M+Na)$^+$ 267; Known Compound, Lit. G. Yang, C. Shen, L. Zhang, W. Zhang. *Tetrahedron Lett.* 2011, 52, 5032.

Example 7

Diethyl benzo[d][1,3]dioxol-5-ylphosphonate (6)

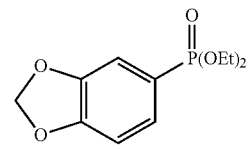

6-(trimethylsilyl)benzo[d][1,3]dioxol-5-yl trifluoromethanesulfonate (25 mg, 0.073 mmol), Cesium Fluoride (61 mg, 0.402 mmol), Triethtyl phosphite (48 mg, 0.292 mmol), Acetonitrile (1 ml): Reaction Time: 16 h; Rf: 0.3 (2:3 EtOAc:Pet Ether); Thick oil; 16.0 mg, 85%; $^1$H NMR (500 MHz, CDCl$_3$, TMS) δ 7.38 (dd, J=7.9, 14.0 Hz, 1H), 7.20 (d, J=12.8 Hz, 1H), 6.88 (dd, J=3.4, 7.6 Hz, 1H), 6.03 (s, 2H), 4.17-4.01 (m, 4H), 1.32 (t, J=7.0 Hz, 6H); $^{13}$C NMR (100 MHz, CDCl$_3$, TMS) δ 151.2 (d, J=2.9 Hz), 147.8 (d, J=22.9 Hz), 127.4 (d, J=11.4 Hz), 121.3 (d, J=193.6 Hz), 111.2 (d, J=12.4 Hz), 108.6 (d, J=18.1 Hz), 101.5, 62.0 (d, J=5.7 Hz), 16.3 (d, J=6.7 Hz); $^{31}$P NMR (162 MHz, CDCl$_3$) δ 19.0; Mass (M+Na)+ 281; Known Compound, Lit. G. Yang, C. Shen, L. Zhang, W. Zhang. *Tetrahedron Lett.* 2011, 52, 5032.

Example 8

Diethyl 3,4-difluorophenylphosphonate (7)

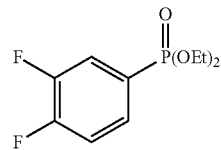

4,5-difluoro-2-(trimethylsilyl)phenyl trifluoromethanesulfonate (25 mg, 0.078 mmol), Cesium Fluoride (62 mg, 0.411 mmol), Triethtyl phosphite (50 mg, 0.299 mmol), Acetonitrile (1 ml): Reaction Time 4 h; Rf: 0.5 (2:3 EtOAc: Pet Ether); Thick oil; 14.6 mg, 78%; $^1$H NMR (500 MHz, CDCl$_3$, TMS) δ 7.67-7.55 (m, 2H), 7.31-7.23 (m, 1H), 4.21-4.05 (m, 4H), 1.34 (t, J=7.0 Hz, 6H); $^{13}$C NMR (125 MHz, CDCl$_3$, TMS) δ 153.1 (ddd, J=3.8, 12.4, 255.6 Hz), 150.2 (ddd, J=13.4, 22.9, 252.7 Hz), 128.8 (ddd, J=3.8, 6.7, 10.5 Hz), 125.9 (dt, J=3.8, 192.7 Hz), 121.1 (dd, J=11.4, 18.1 Hz), 117.9 (t, J=18.1 Hz), 62.4 (d, J=4.8 Hz), 16.2 (d, J=5.7 Hz) $^{31}$P NMR (162 MHz, CDCl$_3$) δ 15.8 (apparent t, J$_{PF}$=6.1 Hz); HRMS-ESI (m/z) calcd (C$_{10}$H$_{13}$F$_2$O$_3$P+H)$^+$: 251.0643. found: 251.0643.

Example 9

Dimethyl 3,4-difluorophenylphosphonate (8)

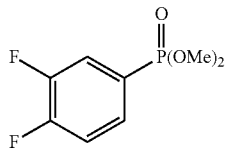

4,5-difluoro-2-(trimethylsilyl)phenyl trifluoromethanesulfonate (25 mg, 0.074 mmol), Cesium Fluoride (62 mg, 0.411 mmol), Trimethtyl phosphite (37 mg, 0.299 mmol), Acetonitrile (1 ml): Reaction Time: 4 h; Rf: 0.4 (1:3 EtOAc: Pet Ether); Thick oil; 11.8 mg, 71%; $^1$H NMR (400 MHz, CDCl$_3$, TMS) δ 7.67-7.53 (m, 2H), 7.34-7.24 (m, 1H), 3.79 (s, 3H), 3.77 (s, 3H); $^{13}$C NMR (100 MHz, CDCl$_3$, TMS) δ 153.3 (ddd, J=3.9, 12.3, 256.6 Hz), 150.3 (ddd, J=12.3, 22.4, 252.0 Hz), 129.0 (ddd, J=3.9, 6.9, 10.8 Hz), 124.2 (dt, J=3.9, 193.4 Hz), 121.3 (dd, J=11.6, J=18.5 Hz), 118.0 (t, J=17.7 Hz), 52.9 (d, J=6.2 Hz); $^{31}$P NMR (162 MHz, CDCl$_3$) δ 18.6 (d, J$_{PF}$=7.5 Hz); HRMS-ESI (m/z) calcd (C$_8$H$_9$F$_2$O$_3$P+H)$^+$: 223.0330. found: 223.0335.

Example 10

Diethyl naphthalen-2-ylphosphonate (9)

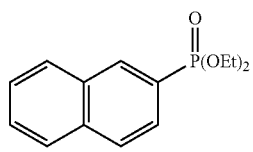

1-(trimethylsilyl)naphthalen-2-yl trifluoromethanesulfonate (25 mg, 0.073 mmol), Cesium Fluoride (60 mg, 0.395 mmol), Triethtyl phosphite (47 mg, 0.287 mmol), Acetonitrile (1 ml): Reaction Time 24 h; Rf: 0.3 (1:3 EtOAc: Pet. Ether); Thick oil; 15.5 mg, 82%; $^1$H NMR (400 MHz, CDCl$_3$, TMS) δ 8.44 (d, J=15.6 Hz, 1H), 7.97-7.85 (m, 3H), 7.81-7.72 (m, 1H), 7.64-7.52 (m, 2H), 4.26-4.05 (m, 4H), 1.34 (t, J=7.0 Hz, 6H); $^{13}$C NMR (100 MHz, CDCl$_3$, TMS) δ 135.0 (d, J=2.3 Hz), 134.0 (d, J=10.0 Hz), 132.3 (d, J=16.2 Hz), 128.9, 128.3 (d, J=14.7 Hz), 128.2, 127.8, 126.8, 126.4 (d, J=9.2 Hz), 125.3 (d, J=188.1 Hz), 62.1 (d, J=5.4 Hz), 16.3 (d, J=6.2 Hz); $^{31}$P NMR (162 MHz, CDCl$_3$) δ 19.1; Mass (M+Na)$^+$ 287; Known compound, Lit. M. Kalek, A. Ziadi, J. Stawinski, *Org. Lett.* 2008, 10, 4637.

Example 11

Synthesis of Ethyl Diphenylphosphinate (10)

To a stirred solution of CsF (70 mg, 0.46 mmol) in anhydrous acetonitrile (1 mL) was consecutively added o-trimethylsilyl phenyl triflate (25 mg, 0.08 mmol) and diethyl phenyl phosphonite (66 mg, 0.33 mmol). Reaction mixture was allowed to stir at room temperature (30° C.) for 24 hrs. The reaction mixture was concentrated and directly loaded on silica gel column and purified by using solvent gradient of Pet. Ether:Ethyl Acetate (1:1) to yield a colourless liquid phosphinate (15.7 mg, 76%).

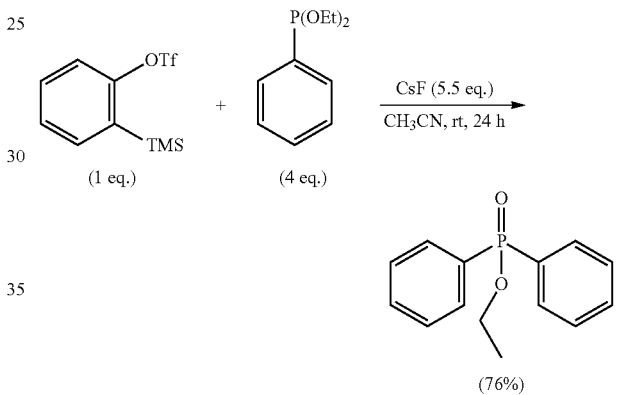

Reaction Time: 24 h; Rf: 0.3 (1:1 EtOAc:Pet Ether); Thick oil; 15.7 mg, 76%; $^1$H NMR (400 MHz, CDCl$_3$, TMS) δ 7.87-7.77 (m, 4H), 7.55-7.48 (m, 2H), 7.47-7.39 (m, 4H), 4.11 (apparent quint, J=7.1 Hz, 2H), 1.37 (t, J=7.1 Hz, 3H); $^{13}$C NMR (100 MHz, CDCl3, TMS) δ 132.0 (d, J=2.1 Hz), 131.6 (d, J=136.4 Hz), 131.5 (d, J=10.1 Hz), 128.4 (d, J=13.1 Hz), 61.1 (d, J=5.4 Hz), 16.4 (d, J=6.2 Hz); 31P NMR (162 MHz, CDCl3) δ 31.3; HRMS-ESI (m/z) calcd (C$_{14}$H$_{15}$O$_2$P+H)$^+$: 247.0882. found: 247.0886; Known compound, Lit. C. Huang, X. Tang, H. Fu, Y. Jiang, Y. Zhao, *J. Org. Chem.* 2006, 71, 5020.

Example 12

Ethyl (2,5-dimethylphenyl)(phenyl)phosphinate (11)

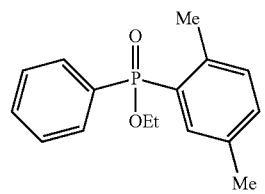 [SMILES: CCOP(=O)(c1ccccc1)c1cc(C)ccc1C]

3,6-dimethyl-2-(trimethylsilyl)phenyl trifluoromethanesulfonate (25 mg, 0.077 mmol), Cesium Fluoride (64 mg, 0.421 mmol), Diethyl phenylphosphonite (60 mg, 0.306 mmol), Acetonitrile (1 ml): Reaction Time: 32 h; Rf: 0.4 (1:1 EtOAc:Pet Ether); Thick oil; 13.0 mg, 62%; $^1$H NMR (400 MHz, CDCl$_3$, TMS) δ 7.81-7.70 (m, 3H), 7.52-7.40 (m, 3H), 7.23 (d, J=7.8 Hz, 1H), 7.12-7.05 (m, 1H), 4.11 (apparent quint, J=7.0 Hz, 2H), 2.36 (s, 3H), 2.33 (s, 3H), 1.38 (t, J=7.0 Hz, 3H); $^{13}$C NMR (100 MHz, CDCl$_3$, TMS) δ 138.6 (d, J=10.8 Hz), 135.0 (d, J=12.3 Hz), 133.9 (d, J=9.3 Hz), 132.5 (d, J=124.1 Hz), 128.4 (d, J=13.4 Hz), 131.7, 131.5 (d, J=7.7 Hz), 131.4, 131.3, 129.0 (d, J=133.3 Hz), 128.4 (d, J=13.1 Hz), 60.7 (d, J=5.4 Hz), 20.9, 20.7 (d, J=3.9 Hz), 16.4 (d, J=6.9 Hz); $^{31}$P NMR (162 MHz, CDCl$_3$,) δ 32.2; HRMS-ESI (m/z) calcd (C$_{16}$H$_{19}$O$_2$P+H)$^+$: 275.1195. found: 275.1193.

Example 13

(2,5-dimethylphenyl)diphenylphosphine oxide (12)

To a stirred solution of CsF (63 mg, 0.42 mmol) in anhydrous acetonitrile 1 mL was consecutively added 2,5 dimethyl-(o-trimethyl silyl)phenyl triflate (25 mg, 0.077 mmol) and ethoxydiphenylphosphine (60 mg, 0.31 mmol). Reaction mixture was allowed to stir at room temperature (30° C.) for 30 hrs. The reaction mixture was concentrated and directly loaded on silica gel column and purified by using solvent gradient of Pet. Ether:Ethyl Acetate (1:1) to yield a white solid phosphine oxide (19 mg, 81%).

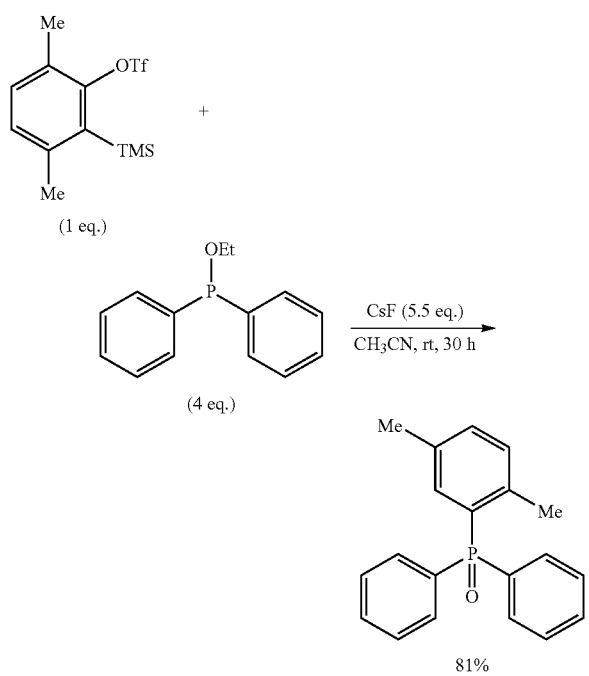

Reaction Time: 30 h; Rf: 0.3 (1:1 EtOAc:Pet Ether); White Solid; mp 157-159° C.; 19.0 mg, 81%; 1H NMR (400 MHz, CDCl3, TMS) δ 7.75-7.60 (m, 4H), 7.59-7.52 (m, 2H), 7.51-7.43 (m, 4H), 7.26-7.20 (m, 1H), 7.19-7.13 (m, 1H), 6.88 (d, J=14.4 Hz, 1H), 2.37 (s, 3H), 2.21 (s, 3H); 13C NMR (100 MHz, CDCl3, TMS) δ 140.0 (d, J=7.7 Hz), 134.7 (d, J=13.1 Hz), 133.9 (d, J=12.3 Hz), 132.9 (d, J=103.3 Hz), 132.8 (d, J=2.3 Hz), 131.9 (d, J=10.0 Hz), 131.8, 131.7 (d, J=3.1 Hz), 130.4 (d, J=103.3 Hz), 128.5 (d, J=11.6 Hz), 21.2 (d, J=4.6 Hz), 21.0; 31P NMR (162 MHz, CDCl3) δ 31.7; HRMS-ESI (m/z) calcd (C20H19OP+H)+: 307.1246. found: 307.1244.

Example 14

Synthesis of (3-methoxyphenyl)diphenylphosphine oxide (13)

To a stirred solution of CsF (64 mg, 0.42 mmol) in anhydrous acetonitrile was consecutively added 2-methoxy(o-trimethyl silyl)phenyl triflate (25 mg, 0.077 mmol) and ethoxydiphenylphosphine (61 mg, 0.31 mmol). Reaction mixture was allowed to stir at room temperature (30° C.) for 20 hrs. The reaction mixture was concentrated and directly loaded on silica gel column and purified by using solvent gradient of Pet. Ether:Ethyl Acetate (1:1) to yield a white sticky solid phosphine oxide (16 mg, 68%).

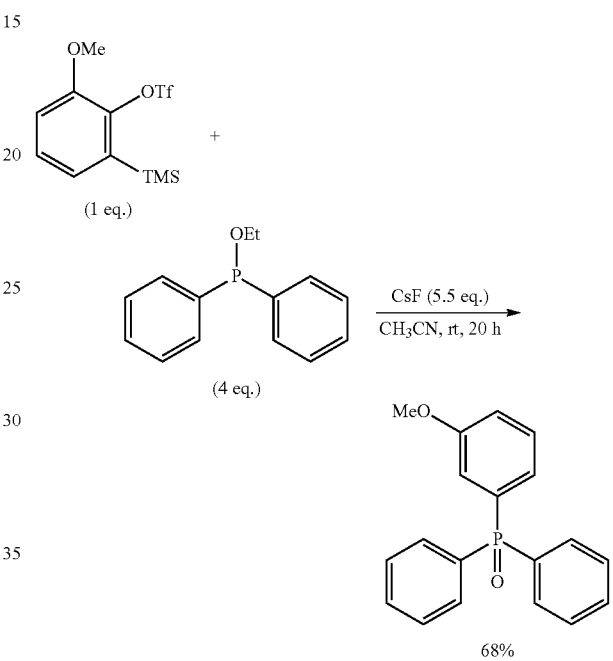

Reaction Time: 20 h; Rf: 0.3 (1:1 EtOAc:Pet Ether); Thick oil; 16.0 mg, 68%; $^1$H NMR (400 MHz, CDCl$_3$, TMS) δ 7.71-7.63 (m, 4H), 7.59-7.52 (m, 2H), 7.50-7.43 (m, 4H), 7.40-7.29 (m, 2H), 7.18-7.05 (m, 2H), 3.80 (s, 3H); $^{13}$C NMR (100 MHz, CDCl$_3$, TMS) δ 159.6 (d, J=15.4 Hz), 133.8 (d, J=103.3 Hz), 132.4 (d, J=104.0 Hz), 132.1 (d, J=10.0 Hz), 131.9 (d, J=3.1 Hz), 129.6 (d, J=14.6 Hz), 128.5 (d, J=12.3 Hz), 124.4 (d, J=10.0 Hz), 118.2 (d, J=3.1 Hz), 116.7 (d, J=10.8 Hz), 55.4; $^{31}$P NMR (162 MHz, CDCl$_3$) δ 29.5; HRMS-ESI (m/z) calcd (C$_{19}$H$_{17}$O$_2$P+H)$^+$: 309.1039. found: 309.1034; Known compound, Lit. X. Zhang, H. Liu, X. Hu, G. Tang, J. Zhu, Y. Zhao, *Org. Lett.* 2011, 13, 3478.

Example 15

Triphenylphosphine Oxide (14)

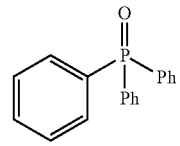

2-(trimethylsilyl)phenyl trifluoromethanesulfonate (25 mg, 0.083 mmol), Cesium Fluoride (70 mg, 0.461 mmol), Ethoxydiphenylphosphane (78 mg, 0.33 mmol), Acetonitrile (1 ml): Reaction Time: 16 h; Rf: 0.3 (1:3 EtOAc:Pet Ether); White Solid; 17.5 mg, 75%; $^1$H NMR (400 MHz, CDCl$_3$, TMS) δ 7.74-7.63 (m, 6H), 7.59-7.51 (m, 3H), 7.50-7.40 (m, 6H); $^{13}$C NMR (100 MHz, CDCl$_3$, TMS) δ 132.5 (d, J=104.0 Hz), 132.1 (d, J=10.0 Hz), 131.9 (d, J=2.3 Hz); 128.5 (d, J=12.4 Hz); $^{31}$P NMR (162 MHz, CDCl$_3$) δ 29.2; Mass (M+Na)$^+$ 301; Known Compound, Lit. K. Prokop, D. Goldberg, *J. Am. Chem. Soc.* 2012, 134, 8014.

Example 16

Naphthalen-2-yldiphenylphosphine oxide (15)

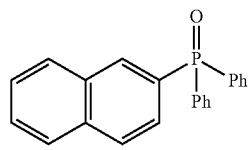

1-(trimethylsilyl)naphthalen-2-yl trifluoromethanesulfonate (25 mg, 0.071 mmol), Cesium Fluoride (60 mg, 0.395 mmol), Ethoxydiphenylphosphane (68 mg, 0.287 mmol), Acetonitrile (1 ml): Reaction Time: 16 h; Rf: 0.4 (1:3 EtOAc:Pet Ether); Thick oil; 19.5 mg, 83%; $^1$H NMR (400 MHz, CDCl$_3$, TMS) δ 8.28 (d, J=13.8 Hz, 1H), 7.95-7.84 (m, 3H), 7.79-7.40 (m, 13H); $^{13}$C NMR (100 MHz, CDCl$_3$, TMS) δ 134.7 (d, J=2.3 Hz), 134.0 (d, J=9.3 Hz), 133.0, 132.3, 132.1 (d, J=10.0 Hz), 132.0 (d, J=1.5 Hz), 131.3 (d, J=243.5 Hz), 128.9, 128.5 (d, J=12.3 Hz), 128.4, 128.2, 127.4 (d, J=87.9 Hz), 126.8 (d, J=10.8 Hz); $^{31}$P NMR (162 MHz, CDCl$_3$) δ 29.3; HRMS-ESI (m/z) calcd (C$_{22}$H$_{17}$OP+H)$^+$: 329.1090. found: 329.1086; Known compound, Lit. Y. -L. Zhao, G. -J. Wu, Y. Li, L. -X. Gao, F.-S. Han, *Chem. Eur. J.* 2012, 18, 9622.

ADVANTAGES OF THE INVENTION

1. Raw materials are commercially available and inexpensive
2. One pot process
3. Room temperature process
4. The process is useful in generating chiral phosphine oxides under mild conditions that can serve as precursors to obtain novel aryl-phosphine ligands useful in organic synthesis.

We claim:

1. A one pot process for the preparation of aryl phosphorous compound of formula (I) comprising reacting o-(trimethylsilyl) aryl triflates (formula II) with phosphorous compound of formula (III) in presence of CsF in polar solvent under stirring for a period ranging between 4-35 h, concentrating and purifying to obtain aryl phosphorous compound of formula (I);

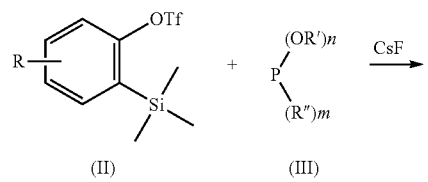

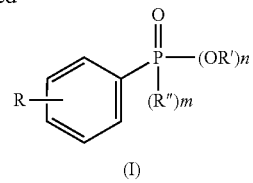

wherein, R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O—; N—R R' and R" represent alkyl, benzyl, alkenyl, alkynyl, (un)substituted or substituted aryl, (un)substituted or substituted heteroaryl;

'n' is 0-2; 'm' is 0-2;

with the proviso, when 'm' is 0, 'n' is 2; R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O, N—R and R' represent alkyl, benzyl, alkenyl, alkynyl, (un)substituted or substituted aryl, (un)substituted or substituted heteroaryl;

with the proviso, when 'n' is 1, 'm' is 1; R represents hydrogen, alkyl, alkenyl, alkynyl, halo, hydroxy, alkoxy, (un)substituted or substituted aryl, benzyl, (un)substituted or substituted heteroaryl, oxalane group, —O—CH$_2$—CH$_2$—O, N—R and R" represent alkyl, benzyl, alkenyl, alkynyl, (un)substituted or substituted aryl, (un)substituted or substituted heteroaryl;

with the proviso, when 'n' is 0, 'm' is 2; R represents hydrogen, alkyl, alkenyl, alkynyl, halo, hydroxy, alkoxy, (un)substituted or substituted aryl, benzyl, (un)substituted or substituted heteroaryl, oxalane group, —O—CH2—CH2—O, N—R and R" represent alkyl, benzyl, alkenyl, alkynyl, (un)substituted or substituted aryl, (un)substituted or substituted heteroaryl.

2. The process as claimed in claim 1, wherein the aryl phosphorous compounds of formula (I) represented by following structures;

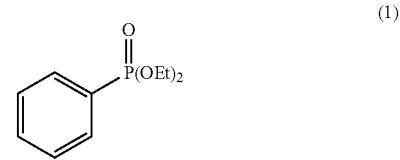

Diethyl phenylphosphonate

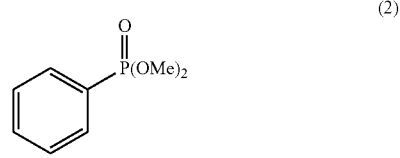

Dimethyl phenylphosphonate

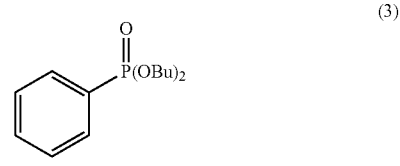

Dibutyl phenylphosphonate (4)
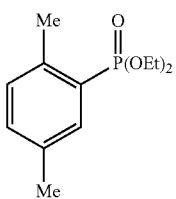
Diethyl 2,5-dimethylphenylphosphonate (5)
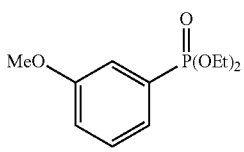
Diethyl 3-methoxyphenylphosphonate (6)
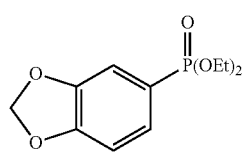
Diethyl benzo[d][1,3]dioxol-5-ylphosphonate (7)
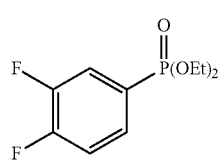
Diethyl 3,4-difluorophenylphosphonate (8)
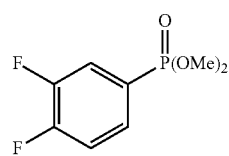
Dimethyl 3,4-difluorophenylphosphonate (9)
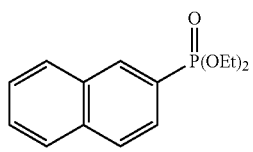
Diethyl naphthalen-2-ylphosphonate

(10)
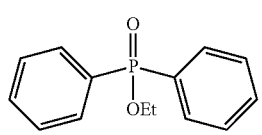
Ethyl diphenylphosphinate

(11)
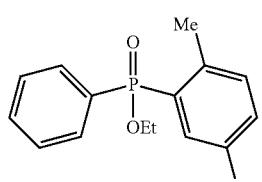
Ethyl(2,5-dimethylphenyl(phenyl)phosphinate

(12)
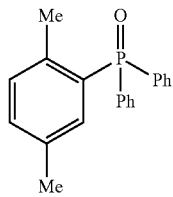
(2,5-dimethylphenyl)diphenylphosphine oxide)

(13)
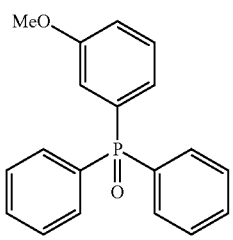
(3-methoxyphenyl)diphenylphosphine oxide

(14)
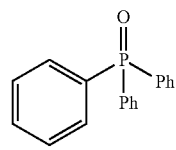 [SMILES: O=P(c1ccccc1)(c1ccccc1)c1ccccc1]
Triphenylphosphine oxide

(15)
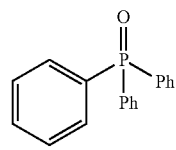 [SMILES: O=P(c1ccccc1)(c1ccccc1)c1ccccc1]
Naphthalen-2-yldiphenylphosphine oxide

3. The process as claimed in claim 1, wherein mole ratio of o-(trimethylsilyl) aryl triflates (formula II) and phosphorous compound of formula (III) is in the range of 1:4.

4. The process as claimed in claim 1, wherein polar solvent used is selected from the group consisting of acetonitrile, Tetrahydrofuran (THF), 1,4-Dioxane, dichloromethane, dichloroethane, butyronitrile, N,N-Dimethylformamide.

5. The process as claimed in claim 1, wherein said process is carried out at a temperature in the range of 25-35° C.

6. The process as claimed in claim 1, wherein yield of aryl phosphorous compounds of formula (I) is in the range of 62-96%.

7. The process as claimed in claim 1, wherein said process is transition-metal-free.

8. The process as claimed in claim 1, wherein said process further comprises generating an aryne intermediate in situ.

* * * * *